United States Patent [19]

Hagen et al.

[11] 4,270,007
[45] May 26, 1981

[54] PERFUME ALDEHYDES FROM HYDROFORMYLATION OF CARYOPHYLLENE

[75] Inventors: Jens Hagen, Ketsch; Klaus Bruns, Krefeld-Traar, both of Fed. Rep. of Germany

[73] Assignee: Henkel Kommanditgesellschaft auf Aktien, Düsseldorf-Holthausen, Fed. Rep. of Germany

[21] Appl. No.: 94,278

[22] Filed: Nov. 14, 1979

[30] Foreign Application Priority Data

Nov. 16, 1978 [DE] Fed. Rep. of Germany ....... 2849720

[51] Int. Cl.³ .................... C07C 47/445; C07C 45/50
[52] U.S. Cl. .................................. 568/445; 568/444; 252/522 R
[58] Field of Search ................ 260/598; 568/445, 444

[56] References Cited

U.S. PATENT DOCUMENTS

| | | | |
|---|---|---|---|
| 2,499,932 | 3/1970 | Pruett et al. | 260/598 |
| 2,880,241 | 3/1959 | Hughes | 260/598 X |
| 3,239,566 | 3/1966 | Slaugh et al. | 260/598 X |

Primary Examiner—Bernard Helfin
Attorney, Agent, or Firm—Hammond & Littell, Weissenberger & Muserlian

[57] ABSTRACT

This invention is directed to mixtures of aldehydes of formulas

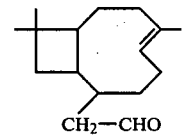

I and

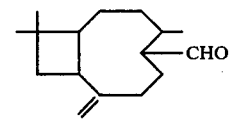

II

This invention is also directed to the preparation of the mixture and the use of said mixture as a perfuming agent.

1 Claim, No Drawings

PERFUME ALDEHYDES FROM HYDROFORMYLATION OF CARYOPHYLLENE

FIELD OF THE INVENTION

The invention is directed to novel aldehydes. More specifically, this invention is directed to the preparation of novel aldehydes by hydroformylation of caryophyllene and to the use of such aldehydes as perfuming agents.

OBJECTS OF THE INVENTION

It is an object of this invention to provide novel aldehydes.

It is also an object of this invention to provide a method of preparation of such aldehydes.

It is further an object of this invention to provide for the use of such aldehydes as perfuming agents.

These and other objects of the invention will become more apparent in the discussion below.

DESCRIPTION OF THE INVENTION

It has been found that novel aldehydes can be prepared by hydroformylation of caryophyllene, a mixture of sesquiterpenes. The hydroformylation takes place with carbon monoxide and hydrogen at from about 70° to 160° C. and under a pressure of from about 100 to 250 bar. Mixtures of tertiary phosphines and rhodium carbonyl complexes containing such tertiary phosphines are used as catalysts. Suitable tertiary phosphines include trialkyl phosphines wherein the alkyl radicals have from about 1 to 20 carbon atoms, as well as triphenyl phosphines wherein the phenyl radicals may be substituted by alkyl or alkoxy groups with 1 to 4 carbon atoms, triphenyl phosphine being preferred. In the catalyst mixtures the molar number of total phosphine present per gram atom of rhodium is in the range of from about 20 to 200.

The exact composition of the catalytically active rhodium carbonyl complexes is not known. It has been assumed, however, that in the complexes one or more carbonyl ligands have been replaced by phosphine ligands. The actual active rhodium carbonyl complex compound is formed in each case in situ under the hydroformylation conditions. The quantity of rhodium required for this purpose can be supplied to the reaction mixture in the form of suitable rhodium compounds, such as rhodium chloride, rhodium oxide, rhodium salts of fatty acids, rhodium chelates, rhodium carbonyl or dimeric rhodium carbonyl chloride, or mixtures thereof. Preferably the rhodium complexes employed are those in which phosphine is already present in the catalyst mixture as a ligand, the compound $RhCl(CO)[P(C_6H_5)_3]_2$ being especially preferred.

Advantageously, the rhodium compounds are used in quantities, based on the amount of caryophyllene present, of from about 5 to 5000 ppm, preferably from about 15 to 400 ppm, calculated as metal.

The reaction can be carried out in the absence of solvents; however, it has proven expedient to use solvents. Useful solvents include saturated hydrocarbons having from 1 to 8 carbon atoms, such as pentane, hexane, heptane, and cyclohexane; aromatics such as benzene, toluene, and xylene; cyclic ethers such as tetrahydrofuran and dioxane; alcohols such as methanol, ethanol, and isopropanol; and diols such as ethylene glycol and propylene glycol. Preferably the hydroformylation is carried out in a saturated hydrocarbon or cyclic ether.

The reaction mixture is worked up by distillation, which is advantageously carried out in an inert gas atmosphere, such as, for example, a nitrogen atmosphere.

The reaction product resulting from the described hydroformylation of caryophyllene according to this invention constitutes, based on the results of gas chromatography, a mixture of four substances. On the basis of the IR spectroscopic data, it is believed that the four substances comprise the respective possible stereoisomers of the following compounds:

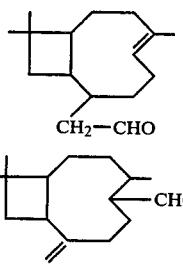

I

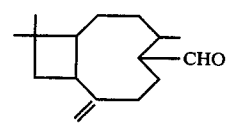

II the two species of Formula II being present in much smaller quantity than those of Formula I.

The mixture of compounds of Formulas I and II has perfume properties and can be mixed with other perfumes in various quantity ratios to provide new perfume compositions. Generally the proportion of the mixture in the perfume compositions will range from about 1 to 50 percent by weight, based on the weight of the total composition. Such compositions can serve directly as perfume or also as perfuming agents in cosmetics, such as creams, lotions, toilet waters, aerosols, toilet soaps, and the like. Also, the mixtures may be used to improve the odor of industrial and commercial products such as detergents and cleansing agents, softeners, textile treatment agents, and the like. To perfume the various products, the perfume compositions containing the mixtures according to the invention are added to the products generally in concentrations of from about 0.05 to 2 percent by weight, based on the total weight of the products.

The following Example is intended to illustrate the invention and is not to be construed as limiting the invention thereto.

EXAMPLE

In a one-liter stroke agitator autoclave of stainless steel, 130 g (0.63 mol) of caryophyllene, 1.9 g (7.25 mmol) of triphenyl phosphine, and 0.1 g (0.145 mmol) of $RhCl(CO)[P(C_6H_5)_3]_2$, were mixed together in 150 ml of tetrahydrofuran. The autoclave was flushed with synthesis gas. Subsequently a gaseous mixture consisting of equal volumes of hydrogen and carbon monoxide was introduced to result in a pressure of 120 bar. The autoclave content was heated to 120° C. with agitation, maintained at from 120° to 130° C. for 6.5 hours, and then cooled to room temperature. The reaction mixture obtained was fractionally distilled under nitrogen atmosphere. After separation of the tetrahydrofuran, 88 g of an aldehyde mixture distilled off at 95° to 110° C. at 0.13 mbar. This represented 60% of theory.

A gas chromatographic test showed that the product constituted a four-component mixture.

Carbonyl number: 110 (theory, 119.7)

The product showed the following IR spectrum (film): 3070 cm$^{-1}$; 2705 cm$^{-1}$; 1725 cm$^{-1}$ (CHO); 1635 cm$^{-1}$ (C=C exocyclic); 1380 cm$^{-1}$ (mixed dimethyl); 1364 cm$^{-1}$; 860 cm$^{-1}$ (C=C trisubstituted).

Odor: Guaiacum note, woody note.

The preceding specific embodiments are illustrative of the practice of the invention. It is to be understood, however, that other expedients known to those skilled in the art, or disclosed herein, may be employed without departing from the spirit of the invention or the scope of the appended claims.

We claim:

1. A mixture consisting essentially of the stereoisomers of the aldehydes

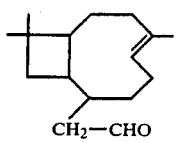

I and

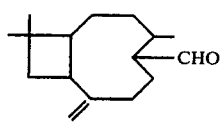

II

* * * * *